(12) United States Patent
Arkwright et al.

(10) Patent No.: US 8,031,988 B2
(45) Date of Patent: Oct. 4, 2011

(54) APPARATUS FOR PRESSURE SENSING

(75) Inventors: John William Arkwright, Ryde (GB);
Simon Nicholas Doe, Burnside (GB);
Vinay Kumar Tyagi, Walkerville (IN);
Edward William Preston, Roseville (GB)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 787 days.

(21) Appl. No.: 11/886,129

(22) PCT Filed: Mar. 9, 2006

(86) PCT No.: PCT/AU2006/000310
§ 371 (c)(1),
(2), (4) Date: Mar. 20, 2008

(87) PCT Pub. No.: WO2006/094353
PCT Pub. Date: Sep. 14, 2006

(65) Prior Publication Data
US 2008/0192230 A1      Aug. 14, 2008

(30) Foreign Application Priority Data

Mar. 10, 2005  (AU) .............................. 2005901143
Jan. 18, 2006  (AU) .............................. 2006900244

(51) Int. Cl.
*G02F 1/295* (2006.01)
*G01L 1/24* (2006.01)
*G01J 1/04* (2006.01)

(52) U.S. Cl. ................ 385/10; 385/12; 385/13; 385/37; 356/35.5; 250/227.14; 250/227.17

(58) Field of Classification Search ................ 385/10, 385/12–13, 37; 600/342
See application file for complete search history.

(56) References Cited

U.S. PATENT DOCUMENTS

| 4,868,495 | A |   | 9/1989  | Einzig et al. |         |
|-----------|---|---|---------|---------------|---------|
| 5,178,153 | A | * | 1/1993  | Einzig ......................... | 600/505 |
| 5,818,982 | A | * | 10/1998 | Voss et al. .................... | 385/13  |

(Continued)

FOREIGN PATENT DOCUMENTS

CN        1632487        6/2005

(Continued)

OTHER PUBLICATIONS

International Search Report, Apr. 19, 2006, from International Patent Application No. PCT/AU2006/000308, filed Mar. 9, 2006.

(Continued)

*Primary Examiner* — Brian M. Healy
*Assistant Examiner* — Guy Anderson
(74) *Attorney, Agent, or Firm* — Sughrue Mion, PLLC

(57) ABSTRACT

The present invention provides an apparatus for pressure sensing. The apparatus comprises a light guide, a Bragg grating incorporated into the light guide and a moveable wall portion. The moveable wall portion has opposite first and second sides and is being positioned so that a change in pressure at one of the sides relative to a pressure at the other side will move the moveable wall portion. The moveable wall portion is coupled to the Bragg grating so that the movement of the moveable wall portion causes a force on a side of the Bragg grating. The force has a component that is transversal to the Bragg grating and effects a change in strain of the Bragg grating and thereby a change in an optical period of the Bragg grating.

22 Claims, 5 Drawing Sheets

U.S. PATENT DOCUMENTS

| | | | |
|---|---|---|---|
| 5,889,901 A * | 3/1999 | Anderson et al. | 385/12 |
| 6,144,026 A * | 11/2000 | Udd et al. | 250/227.14 |
| 6,181,851 B1 | 1/2001 | Pan et al. | |
| 6,205,280 B1 * | 3/2001 | Wagoner et al. | 385/140 |
| 6,218,661 B1 | 4/2001 | Schroeder et al. | |
| 6,304,686 B1 * | 10/2001 | Yamate et al. | 385/13 |
| 6,327,405 B1 * | 12/2001 | Leyva et al. | 385/37 |
| 6,335,998 B2 * | 1/2002 | Wagoner et al. | 385/140 |
| 6,563,970 B1 | 5/2003 | Bohnert et al. | |
| 6,740,047 B2 | 5/2004 | Holmes et al. | |
| 6,898,339 B2 * | 5/2005 | Shah et al. | 385/13 |
| 7,153,299 B1 * | 12/2006 | Tu et al. | 606/15 |
| 7,349,591 B2 * | 3/2008 | Maas | 385/13 |
| 2002/0009252 A1 | 1/2002 | Maron et al. | |
| 2003/0012499 A1 | 1/2003 | Mendez et al. | |
| 2003/0144604 A1 | 7/2003 | Holmes et al. | |
| 2004/0114849 A1 * | 6/2004 | Shah et al. | 385/13 |
| 2004/0237648 A1 | 12/2004 | Jones et al. | |
| 2006/0197012 A1 * | 9/2006 | Udd et al. | 250/227.14 |
| 2008/0192230 A1 | 8/2008 | Arkwright et al. | |
| 2008/0281209 A1 | 11/2008 | Arkwright et al. | |

FOREIGN PATENT DOCUMENTS

| | | |
|---|---|---|
| JP | 2000-097786 | 4/2000 |
| WO | WO 00/33048 | 6/2000 |
| WO | 0033048 A2 | 7/2000 |
| WO | WO 02/19903 | 3/2002 |
| WO | WO 2004/007127 | 1/2004 |

OTHER PUBLICATIONS

International Preliminary Report on Patentability, Jun. 13, 2007, from International Patent Application No. PCT/AU2006/000308, filed Mar. 9, 2006.

International Search Report, Apr. 20, 2006, from International Patent Application No. PCT/AU2006/000309, filed Mar. 9, 2006.

Written Opinion, Apr. 20, 2006, from International Patent Application No. PCT/AU2006/000309, filed Mar. 9, 2006.

International Preliminary Report on Patentability, Jun. 12, 2007, from International Patent Application No. PCT/AU2006/000309, filed Mar. 9, 2006.

Written Opinion, Apr. 19, 2006, from International Patent Application No. PCT/AU2006/000308, filed Mar. 9, 2006.

Written Opinion, Apr. 19, 2006, from International Patent Application No. PCT/AU2006/000310, filed Mar. 9, 2006.

International Search Report, Apr. 19, 2006, from International Patent Application No. PCT/AU2006/000310, filed Mar. 9, 2006.

International Preliminary Report on Patentability, Jan. 30, 2007, from International Patent Application No. PCT/AU2006/000310, filed Mar. 9, 2006.

Supplementary European Search Report for EP06704983, issued Mar. 24, 2011.

* cited by examiner

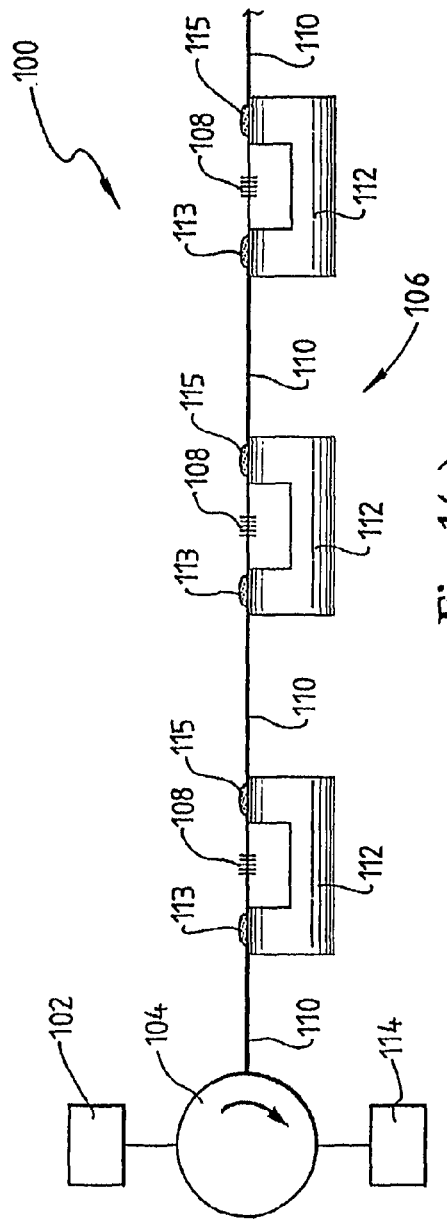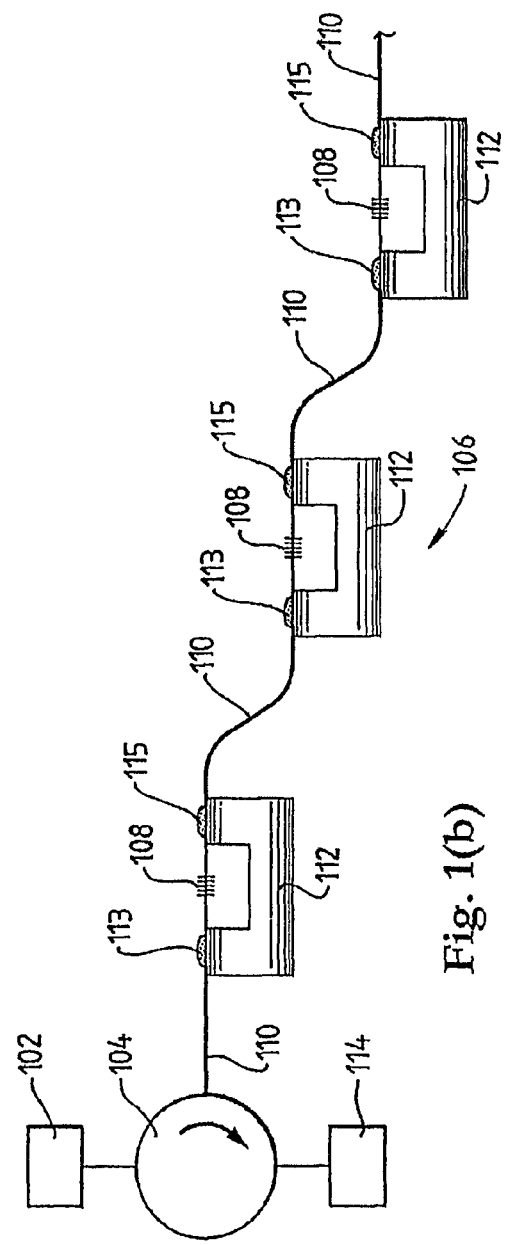

APPARATUS FOR PRESSURE SENSING

FIELD OF THE INVENTION

The present invention broadly relates to an apparatus for pressure sensing.

BACKGROUND OF THE INVENTION

The human body has many regions in which pressure differences cause matter to move. For example, the human heart pumps blood through the body. Muscles around the alimentary canal apply a pressure to the channel which moves food from the mouth into the stomach. Further, a pressure increase in a portion of the body may be caused by a chemical reaction such as the development of a gas in an enclosed body cavity.

Monitoring pressures in the human body can provide important information about the function of the human body and can be used to detect disorders and diseases or can be used to control a recovery from a disease.'

For example, dysphagia, which is a disorder that causes difficulty in swallowing, typically affects infants and elderly people and is especially prevalent in post-stroke patients. It is difficult to diagnose this disease and diagnostic tools are often very uncomfortable for the patient.

A multi-bore catheter tube is commonly used for diagnose of this disorder and the multi-bore catheter is inserted into the oesophagus. The exit ports of the bores of the catheter are positioned at different locations along the catheter and a steady flow of water exits through each port. Measurement of the hydraulic water pressure at an input of each bore gives an indication of the pressure distribution in the oesophagus and therefore can be used to diagnose the disorder.

Another method of in-vivo pressure measurement involves usage of a series of piezoelectric or electro-mechanical devices. Such devices typically are expensive and require a relatively large number of electrical wires to be contained in a catheter which consequently is of relatively large thickness. The device is inserted through the nose of the patient and its relatively large diameter results in discomfort for the patient.

Recently optical pressure measurement devices became popular in which an external pressure change effects a change in light interference conditions which can be detected. Such an optical device may comprise a fibre Bragg grating which has an optical response that depends on a strain of the Bragg grating. Such strain effected by applying a "squeezing" force around the Bragg grating and the resultant increase in strain will shift a wavelength of an optical response to longer wavelengths.

The present invention provides an alternative technical solution.

SUMMARY OF THE INVENTION

The present invention provides in a first aspect an apparatus for pressure sensing, the apparatus comprising:
a light guide,
a Bragg grating incorporated into the light guide, and
a moveable wall portion having opposite first and second sides, the moveable wall portion being positioned so that a change in pressure at one of the sides relative to a pressure at the other side will move the moveable wall portion, the moveable wall portion being coupled to the Bragg grating so that the movement of the moveable wall portion causes a force on the Bragg grating, the force having a component that is transversal to the Bragg grating and being applied from one side of the Bragg grating whereby a change in tensile strain of the Bragg grating is effected.

The apparatus typically comprises an enclosure enclosing a space and which comprises the moveable wall portion. In this case the moveable wall portion typically is positioned so that a change in external pressure causes a change in volume of the enclosed space. The enclosure typically comprises a rigid member which is attached at least two attachment regions to the light guide with the at least one of the Bragg grating and the light guide in a manner so that a sensing region of the Bragg grating is defined between the attachment regions.

The change in strain of the Bragg grating causes a change in an optical response of the Bragg grating to light that is in use guided to the Bragg grating so that the change in strain and hence the change in external pressure can be detected.

The apparatus typically is arranged so that the force on a side portion is applied from one side of the Bragg grating at the sensing region. The apparatus may be arranged so that the force is applied in any transversal or non-axial direction of the Bragg grating, but the apparatus typically is arranged so that the force is applied in a direction that is substantially perpendicular to an axis of the Bragg grating.

The light guide typically is attached to the rigid member at the attachment regions so that the Bragg grating is positioned between the two attachment regions. This arrangement prevents that an axial force acting on the light guide external to the enclosure and the attachment regions affects the optical response of the Bragg grating.

The rigid member of the enclosure typically is a rigid body. The moveable wall portion typically is a diaphragm.

The light guide with the Bragg grating may be directly coupled to the diaphragm. Alternatively, a member that focuses an external pressure related force onto the sensing region of the Bragg grating may be positioned between the Bragg grating and the diaphragm. For example, such a member may be provided in form of an anvil and may increase a sensitivity of the apparatus to changes in the external pressure.

In one specific embodiment the apparatus has a normal operating temperature and pressure range at which the Bragg grating is distorted by the moveable wall portion, typically into the enclosed volume. The apparatus may be arranged so that a temperature related change in a property of the diaphragm, which typically is positioned adjacent the Bragg grating, reduces the temperature related change in the optical response of the Bragg grating. In this embodiment the dual function of the diaphragm, namely reducing a temperature related change in the optical period of the Bragg grating and causing a force on the Bragg grating in response to an external pressure change, facilitates a compact design of the apparatus.

The apparatus may be used for pressure measurements in any environment, including for example in-vivo-environments, laboratories and wind tunnels.

The Bragg grating typically is positioned on the diaphragm and outside the enclosure. Alternatively, the Bragg grating may be positioned within the diaphragm or on the diaphragm and inside the enclosure.

The apparatus may comprise an external catheter that may be arranged for insertion into a human body. Further, the apparatus may comprise a portion comprising an X-ray opaque material which enables imaging the position of the apparatus in the human body.

The moveable wall portion may be positioned opposite a rigid wall portion of the enclosure. In this case the apparatus is suitable for sensing the pressure change on one side of the apparatus. Alternatively, the moveable wall portion may surround a portion of the enclosed volume of the enclosure. In this case the Bragg grating typically also surrounds at least a portion of the enclosed volume.

In another specific embodiment the moveable wall portion and the Bragg grating surround the entire enclosed volume and the apparatus is arranged so that pressure changes can be sensed in a region that radially surrounds the apparatus.

The enclosure typically is filled with a compressible fluid such as air.

The apparatus may be arranged so that the optical response from the Bragg grating can be detected by detecting light that is reflected back from the Bragg grating. In this case the light guide typically is arranged so that the light is guided to and from the Bragg grating by the same optical fibre portion.

The apparatus may also be arranged so that the optical response from the Bragg grating can be detected by detecting light that is transmitted through the Bragg grating. In this case the light guide typically comprises at least one optical fibre for guiding the light to the Bragg grating and at least one other optical fibre for guiding the light from the Bragg grating.

In one specific embodiment of the present invention the apparatus for pressure sensing is one of a plurality of apparatus for pressure sensing, such as a series of the apparatus. The series of the apparatus for pressure sensing typically is arranged for distributed pressure sensing. Each Bragg grating of the series typically is arranged to give a different optical response so that light guided through each Bragg grating is wavelength division multiplexed. With such an apparatus it is possible to detect pressure changes at a series of positions which correspond to the positions of the Bragg gratings. As each Bragg grating gives a different response, it is possible to associate a particular pressure change with a respective position within the body.

In a variation of this embodiment the apparatus also comprises a plurality of the Bragg gratings, but at least some of the Bragg gratings are substantially identical and typically give the same response if the strain conditions are the same. Using time domain reflectometry techniques, the position of a particular Bragg grating may be estimated from a time at which an optical response is received.

In one specific embodiment the apparatus comprises a series of Bragg gratings with corresponding enclosures. In this embodiment each Bragg grating and the light guide comprise one optical fibre which may comprise portions that are spliced together. The optical fibre is attached at the attachment regions to the enclosures associated with respective Bragg gratings, but typically is flexible at regions between adjacent enclosures of the series so that the apparatus is articulated.

The light guide may comprise an optical fibre such as a single mode optical fibre in which the Bragg grating may have been written. As optical fibres are known to cause very little signal loss per length, the apparatus can have a relatively long optical fibre lead and an optical analyser for analysing the response from the or each Bragg grating may be remote from the or each Bragg grating, such as 1 m, 10 m, 1 km or 100 km remote from the or each Bragg grating.

Alternatively, the apparatus may comprise a plurality of Bragg gratings associated with a plurality of respective light guiding arms of the apparatus.

The present invention provides in a second aspect an apparatus for pressure sensing, the apparatus comprising:
a light guide,
a Bragg grating incorporated into the light guide,
an enclosure enclosing a volume and being arranged so that a change in external pressure causes a change in the enclosed volume, the enclosure comprising a moveable wall portion and
a rigid member which is attached at attachment regions to the light guide in a manner so that a sensing region of the Bragg grating is defined between the attachment regions,
wherein the moveable wall portion is coupled to the Bragg grating at the sensing region so that a change in external pressure causes a force on the Bragg grating, the force having a component that is transversal to the Bragg grating and being applied from one side of the Bragg grating whereby a change in tensile strain of the Bragg grating is effected.

The invention will be more fully understood from the following description of specific embodiments of the invention. The description is provided with reference to the accompanying drawings.

BRIEF DESCRIPTION OF THE DRAWINGS

FIGS. 1 (a) and (b) shows a system for distributed pressure sensing according to a specific embodiment of the present invention, FIGS. 2 (a) and (b) show an apparatus for pressure sensing according to an embodiment of the present invention and FIG. 2 (c) shows an alternative component of the apparatus for pressure sensing.

DETAILED DESCRIPTION OF SPECIFIC EMBODIMENTS

Figures 2A, 2B:
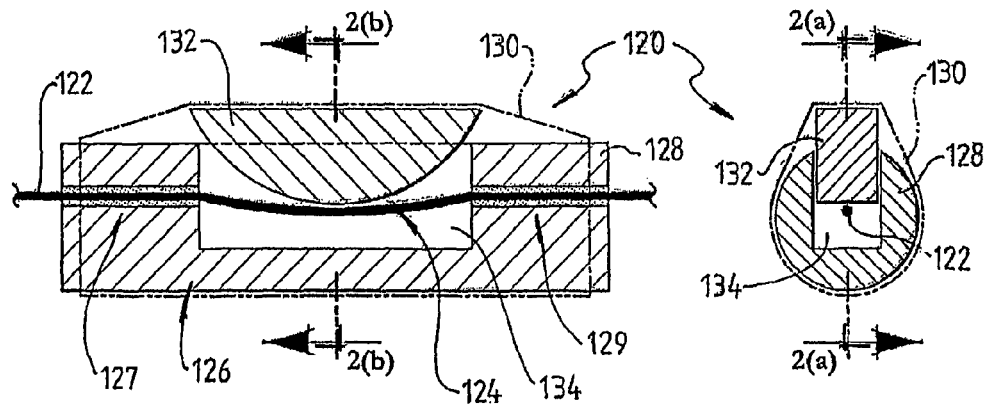

Referring initially to FIG. 1 (a), a system for pressure measurement according to a specific embodiment of the present invention is now described. The system 100 comprises a light source 102 which in this embodiment is a broadband light source commonly referred to as a "white" light source even though the light that is emitted by the light source 102 may have any wavelength range.

The light is directed via optical circulator 104 to an apparatus for pressure sensing 106. In a variation of this embodiment the circulator 104 may be replaced by an optical coupler, an optical splitter or an optical beam splitter.

The apparatus 106 may comprise a catheter (not shown) for insertion into the human body. Further, the apparatus 106 typically comprises an X-ray opaque material, such as a metallic material, for locating the apparatus 106 in the human body.

In this embodiment the apparatus 106 comprises a series of Bragg gratings 108 which are formed in an optical fibre 110. Each Bragg grating 108 is in this embodiment positioned in association with an enclosure 112. Each enclosure 112 has a movable wall portion which is provided in the form of a diaphragm (not shown). In this embodiment, the optical fibre 110 is rigidly connected at end-portions 113 and 115 of a respective enclosure 112 so that a respective Bragg grating 108 is positioned between two end portions. Each Bragg grating is positioned on or near a respective diaphragm such that an external pressure change effects movement of the diaphragm which in turn will apply a strain to the Bragg grating 108. The strain causes a change of an optical property of the Bragg grating 108, such as a change of an optical path length, which influences an optical response of the grating 108 to light guided to the Bragg grating 108. Consequently it is possible to sense a pressure change from analysing the optical response from the Bragg gratings.

It will be appreciated, that in alternative embodiments each Bragg grating 108 may be positioned within or below a respective diaphragm. The remaining walls of the enclosure 112 are formed from a rigid material, such as silicon, a plastics or metallic material (for example stainless steel, invar, tungsten, or kovar), or any other suitable rigid material. In this embodiment the apparatus 106 comprises a series of three Bragg gratings 108. In alternative embodiments the apparatus 106 may comprise any other number of Bragg gratings at any fixed or variable pitch.

In this embodiment each Bragg grating 108 of the series has a slightly different refractive index variation so that each Bragg grating 108 has an optical response that has a slightly different spectral response. The light that is produced by light source 102 and that is directed to the Bragg gratings 108 therefore causes three unique responses from the Bragg gratings 108 which are directed via the optical circulator 104 to optical analyser 114 for optical analysis. Such a procedure is commonly referred to as wavelength division multiplexing (WDM). The Bragg grating may also effect optical responses which overlap in wavelength or frequency space as long as sufficient information is known about each Bragg grating to allow the signals to be successfully deconvolved.

As in this embodiment each Bragg grating 108 causes a different response, it is possible to associate a particular response with a position along the apparatus 106. Consequently it is possible to perform distributed pressure measurements and detect relative pressure difference between the positions of the Bragg gratings 108 in the series. The combined response from the Bragg gratings is wavelength division multiplexed and the optical analyser 114 uses known wavelength division de-multiplexing techniques to identify the responses from the respective grating positions. Suitable software routines are used to determine a pressure or pressure distribution from the optical responses received from the Bragg gratings. Pressure measurements typically include calibrating the apparatus.

In a variation of this embodiment at least some of the Bragg gratings 108 may be identical and consequently, if the strain conditions are the same, their optical response will also be the same. In this case a pulsed light source may be used to guide light to the Bragg gratings and the positions of the Bragg gratings may be estimated from a time at which the responses are received by the optical analyser 114.

In one particular example the reflectivity of each Bragg grating 108 is chosen so that each response has, at the location of the optical analyser 114, approximately the same intensity.

It will be appreciated that in a further variation of this embodiment the apparatus may be arranged so that responses from respective Bragg gratings can be analysed by receiving light that is transmitted through the Bragg gratings 108. For example, in this case the apparatus 106 typically is arranged so that light is guided from the light source 102 through the Bragg gratings 108 and then directly to the optical analyser 114.

In this embodiment each Bragg grating 108 is written into an optical fibre and spliced between fibre portions 110. It will be appreciated, that in alternative embodiments the Bragg gratings 108 and the fibre portions 110 may be integrally formed from one optical fibre. The same optical fibre may be used for writing respective refractive index variations for each grating so that spaced apart Bragg gratings are formed separated by fibre portions. In this embodiment the enclosures 112 comprise a rigid material while the fibre portions 110 are relatively flexible. Consequently the apparatus 106 is an articulated device. FIG. 1 (b) shows the system for pressure sensing 100 also shown in FIG. 1 (a), but the optical fibre 110 is bent between the enclosures 112 of the articulated device.

In variations of this embodiment the apparatus comprises a plurality of Bragg gratings associated with respective optical fibres that are arranged in parallel.

Figure 2C:
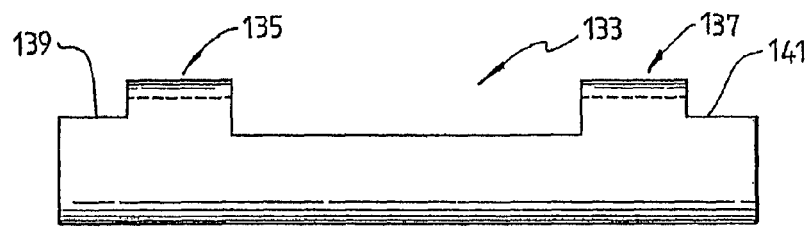

FIGS. 2 (a) and (b) show schematically an apparatus for pressure sensing in more detail. The apparatus 120 comprises an optical fibre 122, a Bragg grating 124 and an enclosure 126 which includes a body 128, a diaphragm 130 and an anvil 132. The optical fibre 122 is attached to the body 128, which is composed of a rigid material, at attachment regions 127 and 129 so that the Bragg grating 124 is positioned between the attachment regions 127 and 129. In this embodiment attachment is effected using a suitable glue but a person skilled in the art will appreciate that various other means may be used to secure the Bragg grating 124 to the body 128. The enclosure 126 encloses a volume 134 and is arranged so that a change in external pressure will change the enclosed volume 134 by deflecting the diaphragm 130 and the anvil 132. This results in a force on the Bragg grating 124 between the attachment regions and from one side which increases a distortion of the Bragg grating 124. In this embodiment the Bragg grating 124 is distorted into the enclosed volume 134. This arrangement prevents that an axial force acting on fibre 122 external to the enclosure and the attachment regions 127 and 129 affects the optical response of the Bragg grating 124.

In the example shown in FIGS. 2 (a) and (b) the distortion of the Bragg grating 124 causes a tensile strain of the Bragg grating 124. If the ambient temperature now increases from the normal operation temperature, a number of physical effects may take place. The optical period of the Bragg grating 124 will typically increase and the enclosed volume 134 will tend to expand. Further, the diaphragm material, which typically is positioned so that the distortion of the Bragg grating is increased at a normal operating temperature, will tend to expand and/or the Young's modulus of the diaphragm material may decrease which in turn causes a decrease of the distorting force on the Bragg grating 124 and thereby counteracts the increase of the optical period. Hence, it is possible to influence the temperature dependency of optical responses by selecting materials having selected thermal behaviour.

Since typically all of the above physical processes influence the grating response as a function of temperature, it is possible to select an enclosure design and a Bragg grating distortion so that the valley of the plot 140 can be shifted to a wide range of temperatures. Further, it would be possible to design the apparatus so that the plot 140 would have more than one valley and/or peak and hence provide an extended range over which acceptable athermal behaviour is achieved.

FIG. 2 (c) shows an enclosure 133 which is a variation of the enclosure 126 shown in FIG. 2 (a). The enclosure 133 has two portions 135 and 137 for securely fixing a fibre containing the Bragg grating and two recesses 139 and 141 for coupling the Bragg grating in a flexible manner. The flexible coupling portions reduce bending forces at the portions 135 and 137 on the coupled Bragg grating.

It is to be appreciated that the apparatus shown in FIG. 2 has only one of many possible designs. For example, the apparatus may not necessarily have an anvil but the Bragg grating may be mechanically distorted into the enclosed volume without an anvil and in contact with the diaphragm.

Figure 4A:
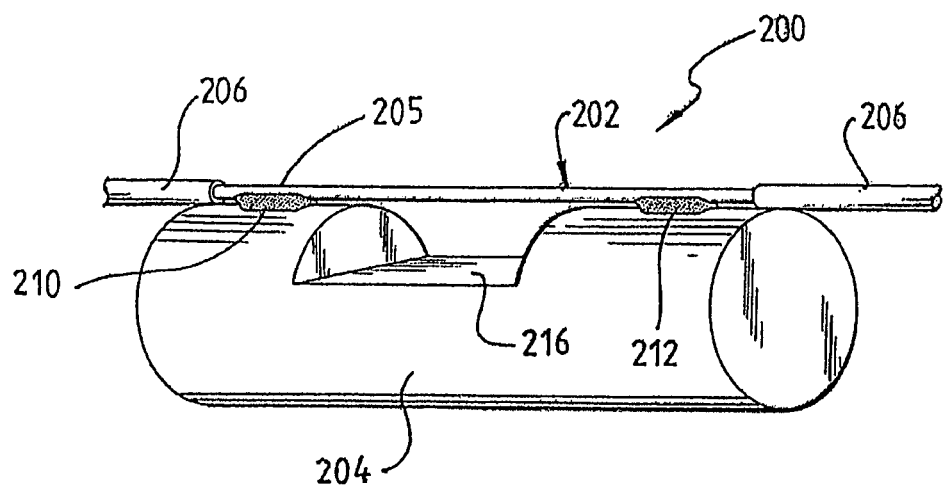
Figure 4B:
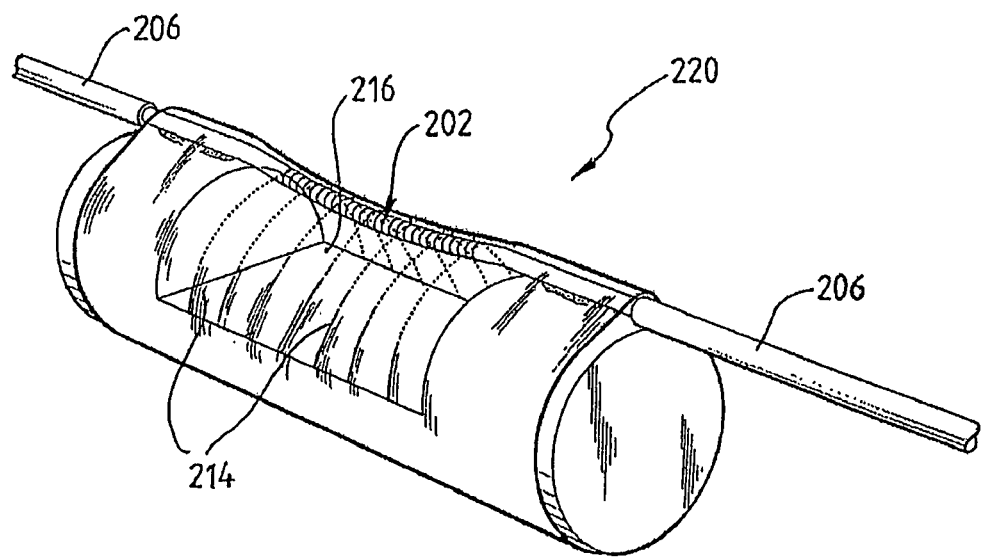

FIGS. 4 (a) and 4 (b) shows an apparatus for pressure sensing according to another embodiment of the present invention. In this embodiment the apparatus 200 comprises a Bragg grating 202 and a body 204. The Bragg grating 202 is formed in an optical fibre that comprises a core/cladding region 205 and a protective coating 206. The protective coating 206 has been stripped away in the area of the Bragg grating 202. The core/cladding region is attached to the body 204. In this embodiment the core/cladding region 205 is glued to the body 204 at regions 210 and 212. For example, the body may be formed from silicon, a plastics or metallic material, or any other suitable rigid material.

FIG. 4 (b) shows an apparatus 220, a variation of the apparatus 200, with a diaphragm 214 applied to it. For example, the diaphragm 214 may be a cold or hot shrink tube which is inserted over the Bragg grating 202 and over the body 204 or an elastic material that stretches around the body 204. As the body 204 has a recess 216, an enclosed pressure sensitive volume is formed at the recess 216 and below the diaphragm 214. The diaphragm 214 is composed of a flexible material such as a rubber or nylon material, a flexible metal foil or silicone foil. Similar to the embodiment shown in FIG. 2, the Bragg grating 202 is slightly distorted into the enclosed volume in the recess 216 (the distortion is shown slightly in FIG. 4 (b) but not in FIG. 4 (a)).

Figure 3:
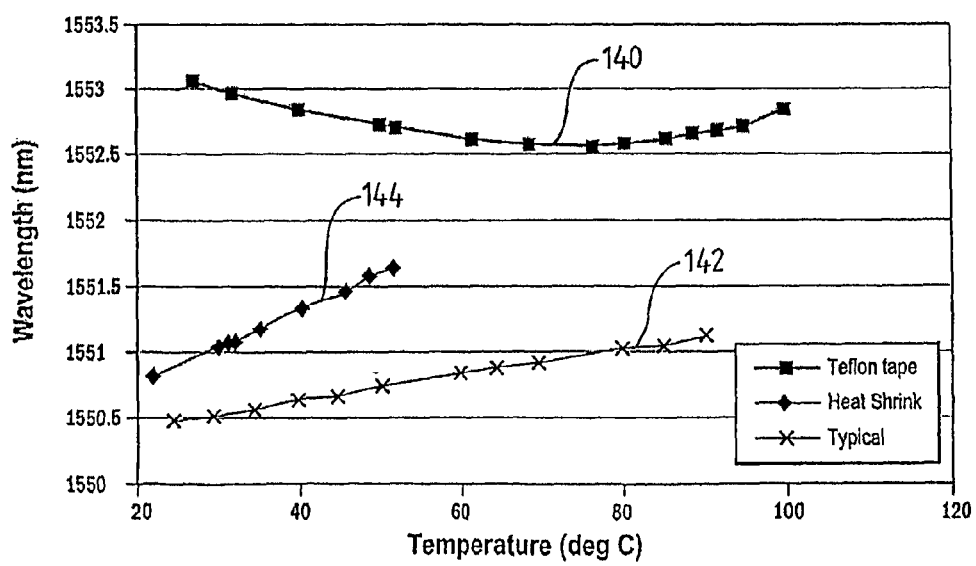
FIG. 3 shows a plot of Bragg grating responses as a function of temperature, FIGS. 4 (a) and (b) shows an apparatus for pressure sensing according to a specific embodiment of the present invention, FIGS. 5 (a) and (b) shows an apparatus for pressure sensing according to a further specific embodiment of the present invention.

FIG. 3 shows plots of Bragg grating responses as a function of temperature. Plot 140 shows the response of a grating of an apparatus for pressure sensing which is schematically shown in FIG. 4. In this example, the enclosure 204 is formed from stainless steel and the diaphragm is formed from polyolefin heat shrink. FIG. 3 shows also a plot 142 for a typical Bragg grating that is not coupled to an enclosure and to a diaphragm and a plot 144 for a Bragg grating bonded to a stainless steel substrate and enclosed by Teflon tape (3M#60 PTFE tape).

An optical response of the Bragg grating typically has a linear dependency on the and on axial strain, but the strain on the fibre in the enclosures described herein typically has a quadratic dependency on the temperature. Consequently, if a Bragg grating 202 is arranged so that a change in temperature of the enclosure 204 also causes a change in strain, the optical response of the Bragg grating 202 will have a combined quadratic and linear dependency on the temperature.

The normal operating temperature of the apparatus 200 is a temperature at which the optical period has a minimum in the valley and by selecting a strain and a distortion applied to the Bragg grating 202 it is possible to select a normal operating temperature having a reduced temperature dependence.

In this example the distortion of the Bragg grating 202 and the design of the enclosure 204 are selected so that the optical response of the Bragg grating does not change by more than approximately 0.001 nm if the temperature changes by ±1 degree from the normal operating temperature of the apparatus centred at approximately 77° C.

In this example the valley is positioned at approximately 77° C., but a person skilled in the art will appreciate that in a variation of this embodiment the apparatus may be designed so that the valley is positioned at approximately 37° C., or normal body temperature, which would then be the normal operating temperature.

Figure 5A:
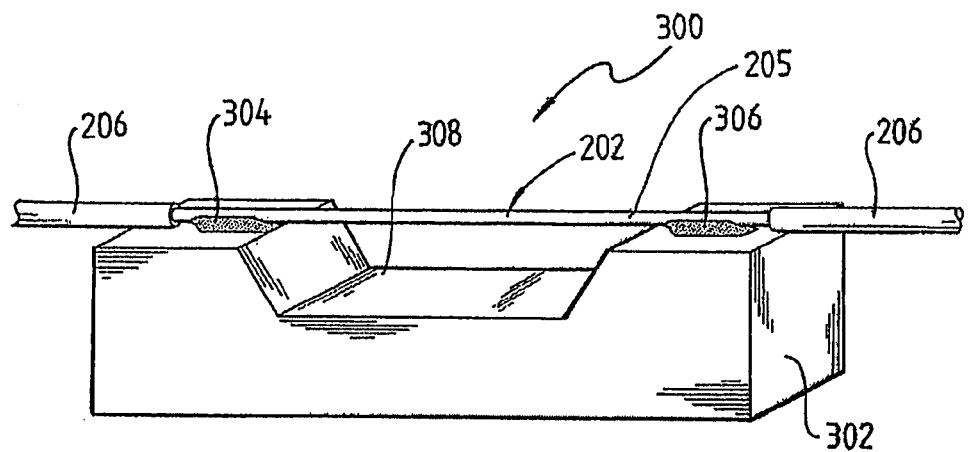
Figure 5B:
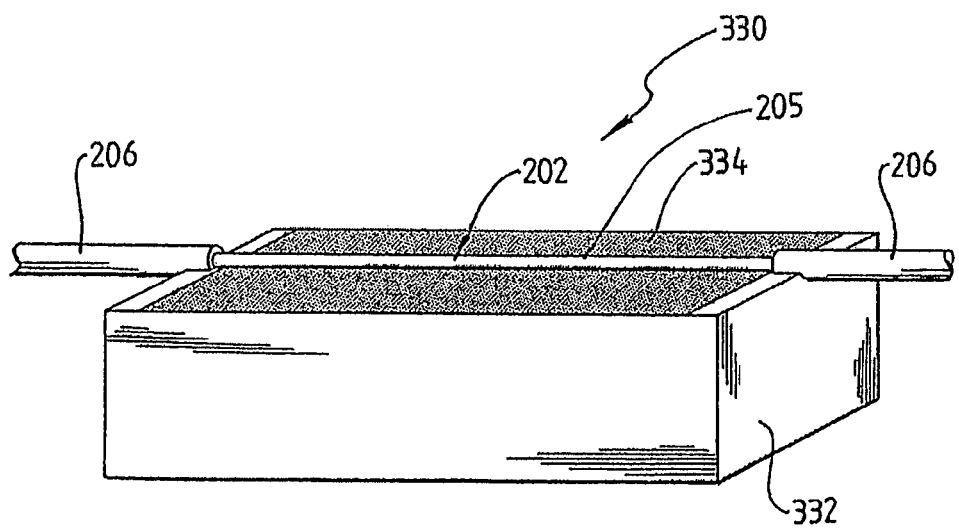

FIGS. 5 (a) and 5 (b) shows apparatus 300 and 330 according to further embodiments of the present invention. Both the apparatus 300 and the apparatus 330 comprise the Bragg grating 202, the fibre core/cladding 205 and the protective coatings 206. The apparatus 300 comprises a body 302 to which the core/cladding region 205 is glued at regions 304 and 306. In this embodiment the body 302 has a substantially rectangular cross sectional area and may be formed from silicon or any other suitable rigid material.

The device 300 further comprises a flexible cover, such as a diaphragm, (not shown) which is positioned over the Bragg grating 202 and encloses recess 308 of the rigid structure 302. Alternatively, the cover may be positioned below the Bragg grating 202 and may cover the recess 308 so that an enclosed internal volume is formed below the Bragg grating 202. In this case the Bragg grating 202 typically is connected to the cover so that a movement of the cover causes a strain to the Bragg grating and consequently a pressure change can be sensed.

The apparatus 330 shown in FIG. 5 (b) comprises a rigid casing 332 which has a flexible cover 334. The casing 332 is hollow and the flexible cover 334 closes the casing 332 to form a hollow internal volume below the Bragg grating 202. As in the previous example, the flexible cover may be a diaphragm. The Bragg grating 302 is attached to the flexible cover so that a movement of the flexible cover will cause a strain in the Bragg grating. The casing 332 typically is composed of a silicon material or of any other suitable rigid material. The flexible cover 334 typically is a thin layer that provides sufficient flexibility and is composed of silicone, another polymeric material or a suitable metallic material.

Figure 6:
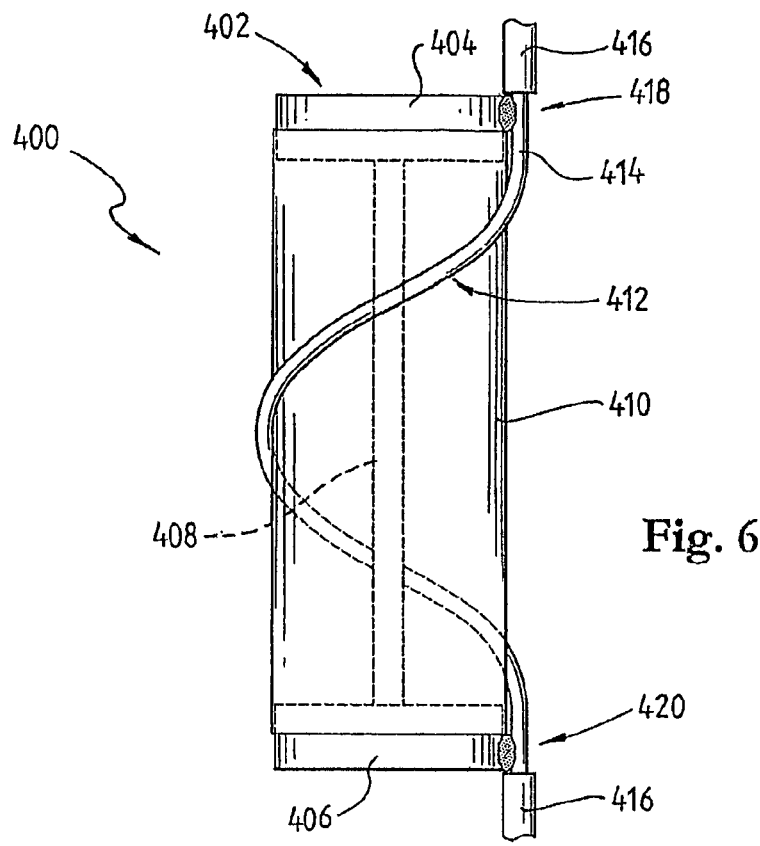
FIG. 6 shows an apparatus for pressure sensing according to another specific embodiment of the present invention and FIG. 7 shows an apparatus for pressure sensing according to yet another specific embodiment of the present invention.

The examples of the apparatus for pressure sensing shown in FIGS. 2, 4 and 5 are suitable for asymmetric pressure sensing. For example, a pressure increase located only at the rigid portions of the casings 304, 303 or 332 will typically not cause a strain to the Bragg gratings 202. FIG. 6 shows an apparatus for pressure sensing according to a further embodiment of the present invention which can be used for more symmetric pressure measurements.

The apparatus 400 comprises a rigid structure 402 having rigid upper and lower portions 404 and 406 and a rigid support portion 408 connecting the upper and lower portions 404 and 406. The rigid support portion is surrounded by a diaphragm 410 which is applied to the upper and lower portions 404 and 406 so that an enclosed internal volume is formed. The apparatus 400 also comprises a Bragg grating 412 and a core/cladding region 414. The core/cladding region 414 is attached to the upper and lower portions 404 and 406 at positions 418 and 420. In this embodiment the core/cladding region is glued at these positions to the upper and lower portions 404 and 406 respectively, and attached to the diaphragm 410.

For example, the Bragg grating 412 may be attached to the diaphragm 410 using a flexible adhesive. If a pressure in a region adjacent the diaphragm 410 changes, the diaphragm 410 will move which will cause a strain in the Bragg grating 412 and therefore the pressure change can be sensed. As the Bragg grating 412 is wound around the diaphragm 410 and the diaphragm 410 surrounds the support 408 so that internal volume is formed between the support 408 and the diaphragm 410, a pressure change can be sensed at any position around the diaphragm 410 using the device 400. Similar to the embodiments discussed before, the Bragg grating 412 is slightly distorted into the enclosed volume (the distortion is not shown in FIG. 6).

The rigid portion 408, the portions 404 and 406 and 404 and the support 408 typically are composed of silicon or of any other suitable rigid material including plastics or metallic materials. The diaphragm 410 typically is a thin layer having a thickness of the order of 0.1 mm being composed of silicone, another polymeric material or a metallic material.

Figure 7:
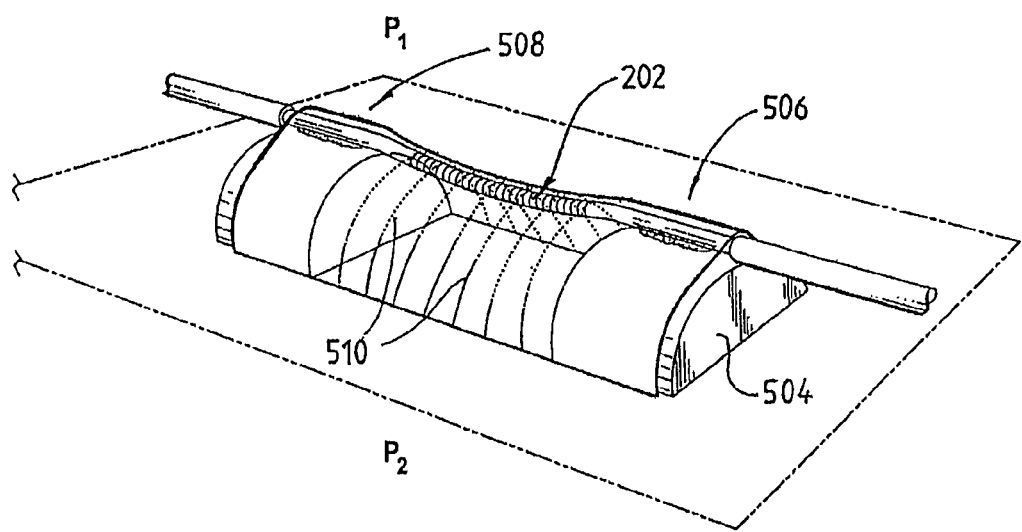

The hereinbefore-described apparatus for pressure sensing according to different embodiments of the present invention comprises an enclosure that defines an enclosed space and of which the diaphragm forms a part. In a variation of these embodiments, the apparatus for pressure sensing may not comprise such an enclosure and FIG. 7 shows an example of such an alternative design. FIG. 7 shows an apparatus for pressure sensing 500 having an optical fibre with the Bragg grating 202 and which is attached to rigid member 504 at attachment regions 506 and 508. Diaphragm 510 distorts the Bragg grating at a normal operating temperature and separates a first region having a first pressure $P_1$ from a second region having a second pressure $P_2$. A relative change in the pressures $P_1$ and $P_2$ will move the diaphragm 510 and thereby cause a change in a force on the Bragg grating 202. As in the above-described embodiments, the diaphragm 510 and the Bragg grating 202 are positioned so that a temperature related change in optical response of the Bragg grating 202 is reduced by a temperature related change in the force on the Bragg grating. For example, the apparatus for pressure sensing 500 may be positioned across a conduit, such as a tube, for measuring a pressure caused by a flow of a fluid.

Although the invention has been described with reference to particular examples, it will be appreciated by those skilled in the art that the invention may be embodied in many other forms. For example, the apparatus for pressure sensing may comprise Bragg gratings that are positioned within the diaphragms. Further, the rigid bodies may have any suitable shape with which an enclosed internal volume can be formed when a diaphragm is applied to it. In addition, the bodies may not be rigid but the apparatus may comprise a separate rigid member to which the optical fibre is attached.

The invention claimed is:

1. An apparatus for pressure sensing, the apparatus comprising:
   a light guide,
   a Bragg grating incorporated into the light guide, and
   a moveable wall portion having opposite first and second sides, the moveable wall portion being positioned so that a change in pressure at one of the sides relative to a pressure at the other side will move the moveable wall portion, the moveable wall portion being coupled to the Bragg grating so that the movement of the moveable wall portion causes a force on the Bragg grating, the force having a component that is transversal to the Bragg grating and being applied from one side of the Bragg grating whereby a movement of the Bragg grating into a space substantially in the direction of the transversal force component and a resultant change in tensile strain of the Bragg grating is effected.

2. The apparatus of claim 1 comprising an enclosure enclosing a space and which comprises the moveable wall portion, the moveable wall portion being positioned so that a change in external pressure causes a change in volume of the enclosed space.

3. The apparatus as claimed in claim 2 comprising a rigid member which is attached at least two attachment regions to the light guide in a manner so that a sensing region of the Bragg grating is defined between the attachment regions.

4. The apparatus as claimed in claim 1 being arranged so that the force on a side portion is applied from one side of the Bragg grating at the sensing region.

5. The apparatus as claimed in claim 1 being arranged so that the force is applied in a direction that is substantially perpendicular to an axis of the Bragg grating.

6. The apparatus as claimed in claim 3 wherein the light guide is attached to the rigid member at the attachment regions so that the Bragg grating is positioned between the two attachment regions in a manner such that an axial force acting on the light guide external to the enclosure and the attachment regions does not affect the optical response of the Bragg grating.

7. The apparatus as claimed in claim 1 wherein the moveable wall portion is a diaphragm.

8. The apparatus as claimed in claim 1 wherein the light guide with the Bragg grating is directly coupled to the moveable wall portion.

9. The apparatus as claimed in claim 1 wherein a member that focuses an external pressure related force onto the sensing region of the Bragg grating is positioned between the Bragg grating and the diaphragm.

10. The apparatus as claimed in claim 9 wherein the member is provided in form of an anvil.

11. The apparatus as claimed in claim 1 having a normal operating temperature and pressure range at which the Bragg grating is distorted by the moveable wall portion prior to application of an external pressure.

12. The apparatus as claimed in claim 1 having a normal operating temperature and pressure range at which the Bragg grating is distorted by the moveable wall portion into the enclosed volume.

13. The apparatus as claimed in claim 1 being arranged so that a temperature related change in optical response of the Bragg grating is reduced by a change in the force on the Bragg grating caused by a temperature related change in the enclosed volume.

14. The apparatus as claimed in claim 1 wherein the Bragg grating is positioned on the diaphragm and outside the enclosure.

15. The apparatus as claimed in claim 1 wherein the Bragg grating is positioned within the diaphragm or on the diaphragm and inside the enclosure.

16. The apparatus as claimed in claim 1 wherein the apparatus is one of a series of apparatus.

17. The apparatus as claimed in claim 15 being arranged for distributed pressure sensing.

18. The apparatus as claimed in claim 16 wherein the series of apparatus comprises a common optical fibre.

19. The apparatus as claimed in claim 17 wherein the optical fibre is attached at the attachment regions, but is flexible at regions between adjacent enclosures of the series so that the apparatus is articulated.

20. An apparatus for pressure sensing, the apparatus comprising:
   a light guide,
   a Bragg grating incorporated into the light guide,
   an enclosure enclosing a volume and being arranged so that a change in external pressure causes a change in the enclosed volume, the enclosure comprising a moveable wall portion and
   a rigid member which is attached at attachment regions to the light guide in a manner so that a sensing region of the Bragg grating is defined between the attachment regions,
   wherein the moveable wall portion is coupled to the Bragg grating at the sensing region so that a change in external pressure causes a force on the Bragg grating, the force having a component that is transversal to the Bragg grating and being applied from one side of the Bragg grating whereby a movement of the Bragg grating into a space substantially in the direction of the transversal force component and a resultant change in tensile strain of the Bragg grating is effected.

21. The apparatus as claimed in claim 1 or 20 comprising an external catheter.

22. The apparatus as claimed in claim 1 or 20 comprising a portion comprising an X-ray opaque material.

* * * * *